(12) United States Patent
Cao et al.

(10) Patent No.: US 8,758,820 B2
(45) Date of Patent: Jun. 24, 2014

(54) ROBUST PELLET

(75) Inventors: Bruce X. Cao, Germantown, MD (US); Beth A. Burnside, Bethesda, MD (US); Sandra E. Wassink, Frederick, MD (US); Matt R. Baker, Frederick, MD (US)

(73) Assignee: Shionogi Inc., Florham Park, NJ (US)

( * ) Notice: Subject to any disclaimer, the term of this patent is extended or adjusted under 35 U.S.C. 154(b) by 1653 days.

(21) Appl. No.: 10/915,912

(22) Filed: Aug. 11, 2004

(65) Prior Publication Data

US 2005/0037071 A1 Feb. 17, 2005

Related U.S. Application Data

(60) Provisional application No. 60/494,155, filed on Aug. 11, 2003.

(51) Int. Cl.
| | |
|---|---|
| *A61K 9/14* | (2006.01) |
| *A61K 9/50* | (2006.01) |
| *A61K 31/43* | (2006.01) |
| *A61K 9/16* | (2006.01) |
| *C07D 499/00* | (2006.01) |

(52) U.S. Cl.
CPC ............ *A61K 9/1617* (2013.01); *C07D 499/00* (2013.01); *A61K 31/43* (2013.01)
USPC ............................ 424/489; 424/502; 514/192

(58) Field of Classification Search
None
See application file for complete search history.

(56) References Cited

U.S. PATENT DOCUMENTS

| | | | | |
|---|---|---|---|---|
| 3,108,046 A | 10/1963 | Harbit | | 167/82 |
| 3,870,790 A | 3/1975 | Lowey et al. | | 424/19 |
| 4,007,174 A | 2/1977 | Laundon | | 260/243 |
| 4,008,246 A | 2/1977 | Ochiai et al. | | 260/306.8 |
| 4,018,918 A | 4/1977 | Ayer et al. | | 514/24 |
| 4,048,306 A | 9/1977 | Maier et al. | | 424/180 |
| 4,131,672 A | 12/1978 | Huffman | | 514/204 |
| 4,175,125 A | 11/1979 | Huffman | | 514/208 |
| 4,226,849 A | 10/1980 | Schor | | 424/19 |
| 4,236,211 A | 11/1980 | Arvesen | | 435/32 |
| 4,250,166 A | 2/1981 | Maekawa et al. | | 424/81 |
| 4,331,803 A | 5/1982 | Watanabe et al. | | 536/7.2 |
| 4,362,731 A | 12/1982 | Hill | | 424/256 |
| 4,369,172 A | 1/1983 | Schor et al. | | 424/19 |
| 4,399,151 A | 8/1983 | Sjoerdsma et al. | | 514/564 |
| 4,430,495 A | 2/1984 | Patt et al. | | 536/16.3 |
| 4,435,173 A | 3/1984 | Siposs et al. | | 609/155 |
| 4,474,768 A | 10/1984 | Bright | | 424/180 |
| 4,517,359 A | 5/1985 | Kobrehel et al. | | 536/7.4 |
| 4,525,352 A | 6/1985 | Cole et al. | | 424/114 |
| 4,529,720 A | 7/1985 | Cole et al. | | 514/191 |
| 4,560,552 A | 12/1985 | Cole et al. | | 424/114 |
| 4,568,741 A | 2/1986 | Livingston | | 536/16.5 |
| 4,598,045 A | 7/1986 | Masover et al. | | 435/34 |
| 4,616,008 A | 10/1986 | Hirai et al. | | 514/200 |
| 4,634,697 A | 1/1987 | Hamashima | | 514/202 |
| 4,644,031 A | 2/1987 | Lehmann et al. | | 524/501 |
| 4,670,549 A | 6/1987 | Morimoto et al. | | 536/7.4 |
| 4,672,109 A | 6/1987 | Watanabe et al. | | 536/7.2 |
| 4,680,386 A | 7/1987 | Morimoto et al. | | 536/7.4 |
| 4,710,565 A | 12/1987 | Livingston et al. | | 536/16.5 |
| 4,723,958 A | 2/1988 | Pope et al. | | 604/890.1 |
| 4,728,512 A | 3/1988 | Mehta et al. | | 424/458 |
| 4,749,568 A | 6/1988 | Reusser et al. | | 424/119 |
| 4,755,385 A | 7/1988 | Etienne et al. | | 424/154 |
| 4,775,751 A | 10/1988 | McShane | | 540/230 |
| 4,794,001 A | 12/1988 | Mehta et al. | | 424/458 |
| 4,808,411 A | 2/1989 | Lu et al. | | 424/441 |
| 4,812,561 A | 3/1989 | Hamashima et al. | | 540/222 |
| 4,828,836 A | 5/1989 | Elger et al. | | 424/419 |
| 4,831,025 A | 5/1989 | Godtfredsen et al. | | 514/195 |
| 4,835,140 A | 5/1989 | Smith et al. | | 514/24 |
| 4,842,866 A | 6/1989 | Horder et al. | | 424/468 |
| 4,849,515 A | 7/1989 | Matier et al. | | 536/16.5 |
| 4,879,135 A | 11/1989 | Greco et al. | | 623/1.48 |
| 4,894,119 A | 1/1990 | Baron, Jr. et al. | | 162/168.2 |
| 4,895,934 A | 1/1990 | Matier et al. | | 536/16.5 |
| 4,904,476 A | 2/1990 | Mehta et al. | | 424/456 |
| 4,915,953 A | 4/1990 | Jordan et al. | | 424/473 |
| 4,945,080 A | 7/1990 | Lindstrom et al. | | 514/29 |
| 4,945,405 A | 7/1990 | Hirota | | 358/516 |
| 4,971,805 A | 11/1990 | Kitanishi et al. | | 424/494 |
| 4,990,602 A | 2/1991 | Morimoto et al. | | 536/7.4 |
| 5,011,692 A | 4/1991 | Fujioka et al. | | 424/426 |
| 5,045,533 A | 9/1991 | Philippe et al. | | 514/29 |
| 5,051,262 A | 9/1991 | Panoz et al. | | 424/468 |
| 5,110,597 A | 5/1992 | Wong et al. | | 424/438 |
| 5,110,598 A | 5/1992 | Kwan et al. | | 424/438 |

(Continued)

FOREIGN PATENT DOCUMENTS

| | | | | |
|---|---|---|---|---|
| EP | 0052075 | 11/1981 | ............... | A61K 9/32 |
| EP | 0293885 | 12/1988 | ............ | C07H 17/08 |

(Continued)

OTHER PUBLICATIONS

Adjei et al., Comparative Pharmacokinetic Study of Continuous Venous Infusion Fluorouracil and Oral Fluorouracil With Eniluracil in Patients with Advanced Solid Tumors, Journal of Clinical Oncology, vol. 20, Issue 6 (Mar. 2002), 1686-1691.

(Continued)

*Primary Examiner* — Robert A Wax
*Assistant Examiner* — Jeffrey T Palenik
(74) *Attorney, Agent, or Firm* — MH2 Technology Law Group, LLP

(57) ABSTRACT

Compositions and methods for making robust pellets that contain a high percentage, by weight, of active drug agent, and which also contain additional components that enhance the absorption and solubility of the active drug agent within the gastrointestinal tract (GI tract) without diminishing the robust nature of the pellet, are disclosed.

16 Claims, No Drawings

(56) References Cited

U.S. PATENT DOCUMENTS

| | | | |
|---|---|---|---|
| 5,143,661 A | 9/1992 | Lawter et al. | 264/4.3 |
| 5,158,777 A | 10/1992 | Abramowitz et al. | 424/458 |
| 5,178,874 A | 1/1993 | Kwan et al. | 424/438 |
| 5,182,374 A | 1/1993 | Tobkes et al. | 536/16.5 |
| 5,204,055 A | 4/1993 | Sachs et al. | 419/2 |
| 5,213,808 A | 5/1993 | Bar-Shalom et al. | 424/473 |
| 5,229,131 A | 7/1993 | Amidon et al. | 424/451 |
| 5,230,703 A | 7/1993 | Alon | 604/20 |
| 5,274,085 A | 12/1993 | Amano et al. | 536/7.4 |
| 5,288,503 A | 2/1994 | Wood et al. | 424/497 |
| 5,334,590 A | 8/1994 | DiNinno et al. | 514/210.09 |
| 5,340,656 A | 8/1994 | Sachs et al. | 428/546 |
| 5,358,713 A | 10/1994 | Shimamura | 424/479 |
| 5,387,380 A | 2/1995 | Cima et al. | 264/69 |
| 5,393,765 A | 2/1995 | Infeld et al. | 514/365 |
| 5,395,626 A | 3/1995 | Kotwal et al. | 424/472 |
| 5,395,628 A | 3/1995 | Noda et al. | 424/490 |
| 5,399,723 A | 3/1995 | Iinuma et al. | 549/403 |
| 5,401,512 A | 3/1995 | Rhodes et al. | 424/458 |
| 5,413,777 A | 5/1995 | Sheth et al. | 424/490 |
| 5,414,014 A | 5/1995 | Schneider et al. | 514/535 |
| 5,422,343 A | 6/1995 | Yamamoto et al. | 514/45 |
| 5,430,021 A | 7/1995 | Rudnic et al. | 514/14 |
| 5,445,829 A | 8/1995 | Paradissis et al. | 424/480 |
| 5,457,187 A | 10/1995 | Gmeiner et al. | 536/25.5 |
| 5,462,747 A | 10/1995 | Radebaugh et al. | 424/465 |
| 5,466,446 A | 11/1995 | Stiefel et al. | 424/78.37 |
| 5,472,708 A | 12/1995 | Chen | 424/451 |
| 5,476,854 A | 12/1995 | Young | 514/254 |
| 5,490,962 A | 2/1996 | Cima et al. | 264/22 |
| 5,508,040 A | 4/1996 | Chen | 424/451 |
| 5,518,680 A | 5/1996 | Cima et al. | 264/401 |
| 5,538,954 A | 7/1996 | Koch et al. | 514/53 |
| 5,543,417 A | 8/1996 | Waldstreicher | 514/284 |
| 5,556,839 A | 9/1996 | Greene et al. | 514/29 |
| 5,567,441 A | 10/1996 | Chen | 424/494 |
| 5,576,022 A | 11/1996 | Yang et al. | 424/472 |
| 5,578,713 A | 11/1996 | McGill, III | 536/18.5 |
| 5,599,557 A | 2/1997 | Johnson et al. | 424/500 |
| 5,607,685 A | 3/1997 | Cimbollek et al. | 424/422 |
| 5,633,006 A | 5/1997 | Catania et al. | 424/441 |
| 5,672,359 A | 9/1997 | Digenis et al. | 424/463 |
| 5,688,516 A | 11/1997 | Raad et al. | 424/409 |
| 5,702,895 A | 12/1997 | Matsunaga et al. | 435/6 |
| 5,705,190 A | 1/1998 | Broad et al. | 424/465 |
| 5,707,646 A | 1/1998 | Yajima et al. | 424/439 |
| 5,719,132 A | 2/1998 | Lin et al. | 514/50 |
| 5,719,272 A | 2/1998 | Yang et al. | 536/7.4 |
| 5,725,553 A | 3/1998 | Moenning | 606/213 |
| 5,733,886 A | 3/1998 | Baroody et al. | 514/24 |
| 5,756,473 A | 5/1998 | Liu et al. | 514/29 |
| 5,780,446 A | 7/1998 | Ramu | 514/34 |
| 5,789,584 A | 8/1998 | Christensen et al. | 540/227 |
| 5,808,017 A | 9/1998 | Chang | 536/7.4 |
| 5,817,321 A | 10/1998 | Alakhov et al. | 424/400 |
| 5,827,531 A | 10/1998 | Morrison et al. | 424/450 |
| 5,837,284 A | 11/1998 | Mehta et al. | 424/459 |
| 5,837,829 A | 11/1998 | Ku | 536/7.4 |
| 5,840,329 A | 11/1998 | Bai | 424/458 |
| 5,840,760 A | 11/1998 | Carraher, Jr. et al. | 514/493 |
| 5,844,105 A | 12/1998 | Liu et al. | 536/18.5 |
| 5,849,776 A | 12/1998 | Czernielewski et al. | 514/398 |
| 5,852,180 A | 12/1998 | Patel | 536/7.4 |
| 5,858,986 A | 1/1999 | Liu et al. | 514/29 |
| 5,864,023 A | 1/1999 | Ku et al. | 536/7.2 |
| 5,869,170 A | 2/1999 | Cima et al. | 428/304.4 |
| 5,872,104 A | 2/1999 | Vermeulen et al. | 514/29 |
| 5,872,229 A | 2/1999 | Liu et al. | 536/18.6 |
| 5,877,243 A | 3/1999 | Sarangapani | 524/139 |
| 5,883,079 A | 3/1999 | Zopf et al. | 514/25 |
| 5,892,008 A | 4/1999 | Ku et al. | 536/18.5 |
| 5,910,322 A | 6/1999 | Rivett et al. | 424/484 |
| 5,919,219 A | 7/1999 | Knowlton | 607/102 |
| 5,919,489 A | 7/1999 | Saleki-Gerhardt et al. | 424/501 |
| 5,919,916 A | 7/1999 | Gracey et al. | 536/7.2 |
| 5,929,219 A | 7/1999 | Hill | 536/7.2 |
| 5,932,710 A | 8/1999 | Liu et al. | 536/18.7 |
| 5,945,124 A | 8/1999 | Sachs et al. | 424/472 |
| 5,945,405 A | 8/1999 | Spanton et al. | 514/29 |
| 5,972,373 A | 10/1999 | Yajima et al. | 424/439 |
| 5,980,942 A | 11/1999 | Katzhendler et al. | 424/465 |
| 5,985,643 A | 11/1999 | Tomasz et al. | 435/243 |
| 5,998,194 A | 12/1999 | Summers, Jr. et al. | 435/252.33 |
| 6,008,195 A | 12/1999 | Selsted | 514/14 |
| 6,010,718 A | 1/2000 | Al-Razzak et al. | 424/464 |
| 6,013,507 A | 1/2000 | Tomasz et al. | 435/252.3 |
| 6,027,748 A | 2/2000 | Conte et al. | 424/458 |
| 6,031,093 A | 2/2000 | Cole et al. | 540/349 |
| 6,048,977 A | 4/2000 | Cole et al. | 540/349 |
| 6,051,255 A | 4/2000 | Conley et al. | 424/482 |
| 6,051,703 A | 4/2000 | Cole et al. | 514/210.06 |
| 6,057,291 A | 5/2000 | Hancock et al. | 514/12 |
| 6,059,816 A | 5/2000 | Moenning | 606/213 |
| 6,063,613 A | 5/2000 | De Lencastre et al. | 435/252.3 |
| 6,063,917 A | 5/2000 | Ascher et al. | 540/217 |
| 6,068,859 A | 5/2000 | Curatolo et al. | 424/490 |
| 6,110,925 A | 8/2000 | Williams et al. | 514/272 |
| 6,117,843 A | 9/2000 | Baroody et al. | 514/24 |
| 6,120,803 A | 9/2000 | Wong et al. | 424/473 |
| 6,127,349 A | 10/2000 | Chasalow | 514/77 |
| 6,132,768 A | 10/2000 | Sachs et al. | 424/458 |
| 6,132,771 A | 10/2000 | Depui et al. | 424/468 |
| 6,136,587 A | 10/2000 | Tomasz et al. | 435/252.3 |
| 6,156,507 A | 12/2000 | Hiramatsu et al. | 435/6 |
| 6,159,491 A | 12/2000 | Durrani | 424/430 |
| 6,162,925 A | 12/2000 | Williams et al. | 548/335.5 |
| 6,183,778 B1 | 2/2001 | Conte et al. | 424/472 |
| 6,187,768 B1 | 2/2001 | Welle et al. | 514/199 |
| 6,214,359 B1 | 4/2001 | Bax | 424/400 |
| 6,218,380 B1 | 4/2001 | Cole et al. | 514/210.06 |
| 6,228,398 B1 | 5/2001 | Devane et al. | 424/484 |
| 6,231,875 B1 | 5/2001 | Sun et al. | 424/401 |
| 6,248,363 B1 | 6/2001 | Patel et al. | 424/497 |
| 6,251,647 B1 | 6/2001 | De Lencastre et al. | 435/193 |
| 6,265,394 B1 | 7/2001 | Sterzycki et al. | 514/203 |
| 6,270,805 B1 | 8/2001 | Chen et al. | 424/497 |
| 6,280,771 B1 | 8/2001 | Monkhouse et al. | 424/484 |
| 6,294,199 B1 | 9/2001 | Conley et al. | 424/468 |
| 6,294,526 B1 | 9/2001 | Higuchi et al. | 514/192 |
| 6,296,873 B1 | 10/2001 | Katzhendler et al. | 424/465 |
| 6,297,215 B1 | 10/2001 | Hancock et al. | 514/12 |
| 6,299,903 B1 | 10/2001 | Rivett et al. | 424/464 |
| 6,306,436 B1 | 10/2001 | Chungi et al. | 424/464 |
| 6,309,663 B1 | 10/2001 | Patel et al. | 424/450 |
| 6,322,819 B1 | 11/2001 | Burnside et al. | 424/494 |
| 6,333,050 B2 | 12/2001 | Wong et al. | 424/473 |
| 6,340,475 B2 | 1/2002 | Shell et al. | 424/469 |
| 6,352,720 B1 | 3/2002 | Martin et al. | 424/464 |
| 6,358,525 B1 | 3/2002 | Guo et al. | 424/464 |
| 6,358,528 B1 | 3/2002 | Grimmett et al. | 424/474 |
| 6,383,471 B1 | 5/2002 | Chen et al. | 424/45 |
| 6,384,081 B2 | 5/2002 | Berman | 514/621 |
| 6,391,614 B1 | 5/2002 | Tomasz et al. | 435/253.2 |
| 6,399,086 B1 | 6/2002 | Katzhendler et al. | 424/405 |
| 6,403,569 B1 | 6/2002 | Achterrath | 514/50 |
| 6,406,717 B2 | 6/2002 | Cherukuri | 424/484 |
| 6,406,880 B1 | 6/2002 | Thornton | 435/32 |
| 6,440,462 B1 | 8/2002 | Raneburger et al. | 424/489 |
| 6,444,796 B1 | 9/2002 | Suh et al. | 536/7.2 |
| 6,468,964 B1 | 10/2002 | Rowe | 514/6 |
| 6,479,496 B1 | 11/2002 | Wolff | 514/252.17 |
| 6,495,157 B1 | 12/2002 | Pena et al. | 424/433 |
| 6,497,901 B1 | 12/2002 | Royer | 424/468 |
| 6,503,709 B1 | 1/2003 | Bekkaoui et al. | 435/6 |
| 6,506,886 B1 | 1/2003 | Lee et al. | 536/7.2 |
| 6,514,518 B2 | 2/2003 | Monkhouse et al. | 424/427 |
| 6,515,010 B1 | 2/2003 | Franchini et al. | 514/411 |
| 6,515,116 B2 | 2/2003 | Suh et al. | 536/7.2 |
| 6,530,958 B1 | 3/2003 | Cima et al. | 623/23.51 |
| 6,541,014 B2 | 4/2003 | Rudnic et al. | 424/400 |
| 6,544,555 B2 | 4/2003 | Rudnic | |
| 6,548,084 B2 | 4/2003 | Leonard et al. | 424/482 |
| 6,550,955 B2 | 4/2003 | D'Silva | 366/130 |

(56) References Cited

U.S. PATENT DOCUMENTS

| | | | |
|---|---|---|---|
| 6,551,584 B2 | 4/2003 | Bandyopadhyay et al. | 424/78.04 |
| 6,551,616 B1 | 4/2003 | Notario et al. | 424/464 |
| 6,558,699 B2 | 5/2003 | Venkatesh | 424/464 |
| 6,565,873 B1 | 5/2003 | Shefer et al. | 424/426 |
| 6,565,882 B2 | 5/2003 | Rudnic | 424/472 |
| 6,569,463 B2 | 5/2003 | Patel et al. | 424/497 |
| 6,585,997 B2 | 7/2003 | Moro et al. | 424/434 |
| 6,599,884 B2 | 7/2003 | Avrutov et al. | 514/29 |
| 6,605,069 B1 | 8/2003 | Albers et al. | 604/264 |
| 6,605,300 B1 | 8/2003 | Burnside et al. | 424/452 |
| 6,605,609 B2 | 8/2003 | Barbachyn et al. | 514/227.8 |
| 6,605,751 B1 | 8/2003 | Gibbins et al. | 602/41 |
| 6,610,323 B1 | 8/2003 | Lundberg et al. | 424/458 |
| 6,610,328 B2 | 8/2003 | Rudnic et al. | 424/468 |
| 6,617,436 B2 | 9/2003 | Avrutov et al. | 536/7.2 |
| 6,623,757 B2 | 9/2003 | Rudnic et al. | 424/468 |
| 6,623,758 B2 | 9/2003 | Rudnic et al. | 424/468 |
| 6,624,292 B2 | 9/2003 | Lifshitz et al. | 536/7.2 |
| 6,627,222 B2 | 9/2003 | Rudnic et al. | 424/468 |
| 6,627,743 B1 | 9/2003 | Liu et al. | 536/7.2 |
| 6,630,498 B2 | 10/2003 | Gudipati et al. | 514/397 |
| 6,632,453 B2 | 10/2003 | Wassink et al. | 424/468 |
| 6,635,280 B2 | 10/2003 | Shell et al. | 424/469 |
| 6,638,532 B2 | 10/2003 | Rudnic et al. | 424/468 |
| 6,642,276 B2 | 11/2003 | Wadhwa | 514/781 |
| 6,663,890 B2 | 12/2003 | Rudnic et al. | 424/468 |
| 6,663,891 B2 | 12/2003 | Rudnic et al. | 424/468 |
| 6,667,042 B2 | 12/2003 | Rudnic et al. | 424/400 |
| 6,667,057 B2 | 12/2003 | Rudnic et al. | 424/468 |
| 6,669,948 B2 | 12/2003 | Rudnic | |
| 6,669,955 B2 | 12/2003 | Chungi et al. | 424/464 |
| 6,673,369 B2 | 1/2004 | Rampal et al. | 424/468 |
| 6,682,759 B2 | 1/2004 | Lim et al. | 424/468 |
| 6,696,426 B2 | 2/2004 | Singh et al. | 514/58 |
| 6,702,803 B2 | 3/2004 | Kupperblatt et al. | 604/890.1 |
| 6,706,273 B1 | 3/2004 | Roessler | 424/422 |
| 6,723,340 B2 | 4/2004 | Gusler et al. | 424/468 |
| 6,723,341 B2 | 4/2004 | Rudnic | |
| 6,730,320 B2 | 5/2004 | Rudnic et al. | 424/468 |
| 6,730,325 B2 | 5/2004 | Devane et al. | 424/469 |
| 6,735,470 B2 | 5/2004 | Henley et al. | 604/20 |
| 6,740,664 B2 | 5/2004 | Cagle et al. | 514/311 |
| 6,746,692 B2 | 6/2004 | Conley et al. | 424/468 |
| 6,756,057 B2 | 6/2004 | Storm et al. | 424/472 |
| 6,767,899 B1 | 7/2004 | Kay et al. | 514/62 |
| 6,777,420 B2 | 8/2004 | Zhi et al. | 514/272 |
| 6,783,773 B1 | 8/2004 | Storm et al. | 424/468 |
| 6,818,407 B2 | 11/2004 | Hancock et al. | 435/7.1 |
| 6,824,792 B2 | 11/2004 | Foreman et al. | 424/487 |
| 6,872,407 B2 | 3/2005 | Notario et al. | 424/464 |
| 6,878,387 B1 | 4/2005 | Petereit et al. | 424/490 |
| 6,906,035 B2 | 6/2005 | Hancock et al. | 514/12 |
| 6,929,804 B2 | 8/2005 | Rudnic et al. | 424/468 |
| 6,946,458 B2 | 9/2005 | Turos | 514/210.15 |
| 6,984,401 B2 | 1/2006 | Rudnic et al. | 424/489 |
| 6,991,807 B2 | 1/2006 | Rudnic et al. | 424/468 |
| 7,008,633 B2 | 3/2006 | Yang et al. | 424/422 |
| 2001/0046984 A1 | 11/2001 | Rudnic | 514/210.09 |
| 2001/0048944 A1 | 12/2001 | Rudnic et al. | 424/468 |
| 2002/0004070 A1 | 1/2002 | Rudnic et al. | 424/468 |
| 2002/0004499 A1 | 1/2002 | Rudnic et al. | 514/192 |
| 2002/0015728 A1 | 2/2002 | Payumo et al. | 424/451 |
| 2002/0028920 A1 | 3/2002 | Lifshitz et al. | 536/7.1 |
| 2002/0042394 A1 | 4/2002 | Hogenkamp et al. | 514/53 |
| 2002/0068078 A1 | 6/2002 | Rudnic et al. | 424/408 |
| 2002/0068085 A1 | 6/2002 | Rudnic et al. | 424/468 |
| 2002/0081332 A1 | 6/2002 | Rampal et al. | 424/461 |
| 2002/0103261 A1 | 8/2002 | Ninkov | 514/731 |
| 2002/0106412 A1 | 8/2002 | Rowe et al. | 424/490 |
| 2002/0115624 A1 | 8/2002 | Behar et al. | 514/42 |
| 2002/0119168 A1 | 8/2002 | Rudnic et al. | 424/400 |
| 2002/0136764 A1 | 9/2002 | Rudnic et al. | 424/457 |
| 2002/0136765 A1 | 9/2002 | Rudnic et al. | 424/457 |
| 2002/0136766 A1 | 9/2002 | Rudnic et al. | 424/457 |
| 2002/0150619 A1 | 10/2002 | Rudnic et al. | 424/468 |
| 2002/0197314 A1 | 12/2002 | Rudnic et al. | 424/468 |
| 2003/0012814 A1 | 1/2003 | Rudnic et al. | 424/468 |
| 2003/0018295 A1 | 1/2003 | Henley et al. | 604/20 |
| 2003/0049311 A1 | 3/2003 | McAllister et al. | 424/452 |
| 2003/0064100 A1 | 4/2003 | Rudnic et al. | 424/468 |
| 2003/0073647 A1 | 4/2003 | Chao et al. | 514/42 |
| 2003/0073648 A1 | 4/2003 | Chao et al. | 514/42 |
| 2003/0073826 A1 | 4/2003 | Chao et al. | 536/18.7 |
| 2003/0077323 A1 | 4/2003 | Rudnic et al. | 424/468 |
| 2003/0086969 A1 | 5/2003 | Rudnic et al. | 424/468 |
| 2003/0091627 A1 | 5/2003 | Sharma | 424/465 |
| 2003/0096006 A1 | 5/2003 | Rudnic et al. | 424/468 |
| 2003/0096007 A1 | 5/2003 | Rudnic et al. | 424/468 |
| 2003/0096008 A1 | 5/2003 | Rudnic et al. | 424/468 |
| 2003/0099706 A1 | 5/2003 | Rudnic et al. | 424/468 |
| 2003/0099707 A1 | 5/2003 | Rudnic et al. | 424/468 |
| 2003/0104054 A1 | 6/2003 | Rudnic et al. | 424/468 |
| 2003/0104055 A1 | 6/2003 | Rudnic et al. | 424/468 |
| 2003/0104056 A1 | 6/2003 | Rudnic et al. | 424/468 |
| 2003/0104058 A1 | 6/2003 | Rudnic et al. | 424/468 |
| 2003/0124196 A1 | 7/2003 | Weinbach et al. | 424/499 |
| 2003/0129236 A1 | 7/2003 | Heimlich et al. | 424/470 |
| 2003/0143268 A1 | 7/2003 | Pryce Lewis et al. | 424/464 |
| 2003/0147953 A1 | 8/2003 | Rudnic et al. | 424/468 |
| 2003/0180352 A1* | 9/2003 | Patel et al. | 424/465 |
| 2003/0190360 A1 | 10/2003 | Baichwal et al. | 424/470 |
| 2003/0198677 A1 | 10/2003 | Pryce Lewis et al. | 424/471 |
| 2003/0199808 A1 | 10/2003 | Henley et al. | 604/20 |
| 2003/0203023 A1 | 10/2003 | Rudnic et al. | 424/468 |
| 2003/0206951 A1 | 11/2003 | Rudnic et al. | 424/468 |
| 2003/0216555 A1 | 11/2003 | Lifshitz et al. | 536/7.1 |
| 2003/0216556 A1 | 11/2003 | Avrutov et al. | 536/7.2 |
| 2003/0232089 A1 | 12/2003 | Singh et al. | 424/488 |
| 2003/0235615 A1 | 12/2003 | Rudnic | 424/468 |
| 2004/0018234 A1 | 1/2004 | Rudnic et al. | 424/468 |
| 2004/0033262 A1 | 2/2004 | Kshirsagar et al. | 424/468 |
| 2004/0043073 A1 | 3/2004 | Chen et al. | 424/486 |
| 2004/0047906 A1 | 3/2004 | Percel et al. | 424/468 |
| 2004/0048814 A1 | 3/2004 | Vanderbist et al. | 514/29 |
| 2004/0052842 A1 | 3/2004 | Rudnic et al. | 424/468 |
| 2004/0058879 A1 | 3/2004 | Avrutov et al. | 514/29 |
| 2004/0091528 A1 | 5/2004 | Rogers et al. | 424/468 |
| 2004/0126427 A1 | 7/2004 | Venkatesh et al. | 424/469 |
| 2004/0176737 A1 | 9/2004 | Henley et al. | 604/501 |
| 2004/0208936 A1* | 10/2004 | Chorin et al. | 424/490 |
| 2004/0219223 A1 | 11/2004 | Kunz | 424/489 |
| 2004/0253249 A1 | 12/2004 | Rudnic et al. | 424/184.1 |
| 2004/0265379 A1 | 12/2004 | Conley et al. | 424/465 |
| 2005/0053658 A1 | 3/2005 | Venkatesh et al. | 424/468 |
| 2005/0064033 A1 | 3/2005 | Notario et al. | 424/468 |
| 2005/0064034 A1 | 3/2005 | Li et al. | 424/469 |
| 2005/0163857 A1 | 7/2005 | Rampal et al. | 424/489 |
| 2005/0203076 A1 | 9/2005 | Li et al. | 514/183 |
| 2005/0203085 A1 | 9/2005 | Li et al. | 514/224.5 |
| 2005/0209210 A1 | 9/2005 | Ding et al. | 514/183 |
| 2005/0238714 A1 | 10/2005 | Rudnic et al. | 424/468 |
| 2005/0256096 A1 | 11/2005 | Combrink et al. | 514/183 |
| 2005/0261262 A1 | 11/2005 | Ma et al. | 514/183 |
| 2005/0277633 A1 | 12/2005 | Ma et al. | 514/224.5 |
| 2006/0019985 A1 | 1/2006 | Ma et al. | 514/306 |
| 2006/0019986 A1 | 1/2006 | Ding et al. | 514/306 |
| 2006/0111302 A1 | 5/2006 | Romesberg et al. | 514/18 |

FOREIGN PATENT DOCUMENTS

| | | | | |
|---|---|---|---|---|
| EP | 0436370 | 7/1991 | | A61K 9/54 |
| EP | 0652008 | 5/1995 | | A61K 31/47 |
| FR | 2585948 | 2/1982 | | A61K 9/22 |
| GB | 2087235 | 5/1982 | | A61K 9/16 |
| WO | WO 90/08537 | 8/1990 | | A61K 31/00 |
| WO | WO 94/27557 | 12/1994 | | |
| WO | WO 95/20946 | 8/1995 | | A61K 9/20 |
| WO | WO 95/30422 | 11/1995 | | A61K 31/71 |
| WO | WO 96/04908 | 2/1996 | | A61K 31/43 |
| WO | WO 97/22335 | 6/1997 | | A61K 9/20 |
| WO | WO 97/43277 | 11/1997 | | A61K 31/505 |
| WO | WO 98/22091 | 5/1998 | | A61K 9/10 |
| WO | WO 98/46239 | 10/1998 | | A61K 31/71 |

(56) References Cited

FOREIGN PATENT DOCUMENTS

| WO | WO 99/03453 | 1/1999 | ............... A61K 9/50 |
|---|---|---|---|
| WO | WO 99/40097 | 8/1999 | ............... C07H 1/00 |
| WO | WO 00/48607 | 8/2000 | ............. A61K 31/70 |
| WO | WO 00/61116 | 10/2000 | ............... A61K 9/20 |
| WO | WO 01/26663 | 4/2001 | ......... A61K 31/7048 |
| WO | WO 02/38577 | 5/2002 | |
| WO | WO 03/029439 | 4/2003 | ............... C12N 1/14 |
| WO | WO 2005/056754 | 6/2005 | |
| WO | WO 2005/070941 | 8/2005 | ........... C07D 498/08 |

OTHER PUBLICATIONS

Andes, Pharmacokinetic and Pharmacodynamic Properties of Antimicrobials in the Therapy of Respiratory Tract Infections, Current Opinion in Infectious Diseases, 14(2):165-172, Apr. 2001. (Abstract).
Auckenthaler, Pharmacokinetics and Pharmacodynamics of Oral Beta-Lactam Antibiotics as a Two-Dimensional Approach to Their Efficacy, J Antimicrob Chemother, (2002) 50, 13-17.
Berry et al., Bacteriological Efficacies of Three Macrolides Compared with Those Amoxicillin-Clavulanate Against *Streptococcus pneumoniae* and *Haemophilus influenzae*, Antimicrob Agents Chemother. Dec. 1998, 42(12): 3193-3199.
Bhargava et al., Pulsed Feeding During Fed-Batch Fungal Fermentation Leads to Reduced Viscosity Without Detrimentally Affecting Protein Expression, Biotechnology and Bioengineering, vol. 81, No. 3, Feb. 5, 2003, pp. 341-347.
Bhargava et al., Pulsed Feeding During Fed-Batch *Aspergillus oryzae* Fermentation Leads to Improved Oxygen Mass Transfer, Biotechnol. Prog. 2003, 19, 1091-1094.
Bhargava et al., Pulsed Addition of Limiting-Carbon During *Aspergillus oryzae* Fermentation Leads to Improved Productivity of a Recombinant Enzyme, Biotechnology and Bioengineering, vol. 82, No. 1, Apr. 5, 2003, pp. 111-117.
Bishai, Comparative Effectiveness of Different Macrolides: Clarithromycin, Azithromycin, and Erythromycin, Johns Hopkins Point of Care Information Technology (POC-IT).
Bradley, *Staphylococcus aureus pneumonia*: Emergence of MRSA in the Community, Semin Respir Crit Care Med. 2005; 26 (6): 643-649.
Brogden et al., Cefixime. A Review of Its Antibacterial Activity. Pharmacokinetic Properties and Therapeutic Potential, Drugs, Oct. 1989; 38 (4): 524-50. (Abstract).
Burgess et al., A Time-Kill Evaluation of Clarithromycin and Azithromycin Against Two Extracellular Pathogens and the Development of Resistance, The Annals of Pharmacotherapy: vol. 33, No. 12, pp. 1262-1265. (Abstract).
Byfield et al., Relevance of the Pharmacology of Oral Tegafur to its Use as a 5-FU Pro-Drug., Cancer Treat Rep. Jun. 1985; 69 (6): 645-52. (Abstract).
Cappelletty et al., Bactericidal Activities of Cefprozil, Penicillin, Cefaclor, Cefixime, and Loracarbef against Penicillin-Susceptible and -Resistant *Streptococcus pneumoniae* in an in Vitro Pharmacodynamic Infection Model, Antimicrobial Agents and Chemotherapy, May 1996, p. 1148-1152.
Cha et al., Pulsatile Delivery of Amoxicillin Against *Streptococcus pneumoniae*, Journal of Antimicrobial Chemotherapy, Advance Access Published Oct. 14, 2004.
Craig, Antibiotic Selection Factors and Description of a Hospital-Based Outpatient Antibiotic Therapy Program in the USA, Eur J Clin Microbiol Infect Dis. Jul. 1995;14(7):636-42. (Abstract).
Cremieux et al., Ceftriaxone Diffusion into Cardiac Fibrin Vegetation. Qualitative and Quantitative Evaluation by Autoradiography, Fundam Clin Pharmacol. 1991;5(1):53-60. (Abstract).
Endo et al., Fungicidal Action of Aureobasidin A, a Cyclic Depsipeptide Antifungal Antibiotic, against *Saccharomyces cerevisiae*, Antimicrobial Agents and Chemotherapy, Mar. 1997, p. 672-676.

Erah et al., The Stability of Amoxycillin, Clarithromycin and Metronidazole in Gastric Juice: Relevance to the Treatment of *Helicobacter pylori* Infection, J Antimicrob Chemother Jan. 1997;39 (1):5-12. (Abstract).
Fang, A Study of the Ethical Considerations and Implications, Prozac Weekly and Sarafem in the Wake of Prozac s Patent Expiration, 5.22J/10.02J, Biotechnology and Engineering.
Feder et al., Once-Daily Therapy for *Streptococcal pharyngitis* Wtih Amoxicillin, American Academy of Pediatrics, vol. 103(1), Jan. 1999, pp. 47-51.
Freeman et al., The Cydosporin-Erythromycin Interaction: Impaired First Pass Metabolism in the Pig, Br J Pharmacol. Jul. 1991;103(3):1709-12. (Abstract).
Frimodt-Moller, Correlation Between Pharmacokinetic / Pharmacodyamic Parameters and Efficacy for Antibiotics in the Treatment of Urinary Tract Infection, Int. J. Antimicrob. Agents, 19 (2002) 546-53.
Furlanut et al., Pharmacokinetic Aspects of Levofloxacin 500mg Once Daily During Sequential Intravenous/Oral Therapy in Patients with Lower Respiratory Tract Infections, Journal of Antimicrobial Chemotherapy (2003) 51, 101-106.
Gill et al., In Vivo Activity and Pharmacokinetic Evaluation of a Novel Long-Acting Carbapenem Antibiotic, MK-826 (L-749, 345), Antimicrobial Agents and Chemotherapy, Aug. 1998;42(8):1996-2001.
Gnarpe et al., Penicillin Combinations Against Multi-Resistant Urinary Pathogens as an Alternative to Gentamycin Treatment, Microbios 1976;16(65-66):201-6. (Abstract).
Gordon et al., Rationale for Single and High Dose Treatment Regimens with Azithromycin, Pediatric Infectious Disease Journal. 23(2) Supplement: S102-S107, Feb. 2004. (Abstract).
Goswick et al., Activities of Azithromycin and Amphotericin B Against *Naegleria fowleri* In Vitro and in a Mouse Model of Primary Amebic Meningoencephalitis, Antimicrob Agents Chemother. Feb. 2003; 47(2): 524-528.
Harbarth et al., Prolonged Antibiotic Prophylaxis After Cardiovascular Surgery and Its Effect on Surgical Site Infections and Antimicrobial Resistance, Circulation Jun. 27, 2000; 101:2916-2921.
Haney, New Drugs Kill Bacteria Resistant to Antibiotics, Called Ketolides, They are Chemically New to the Harmful Bugs, Thursday, Sep. 21, 2000, Seattle Post-Intelligencer.
Harris et al., Esophageal Carcinoma: Curative Treatment, Combined Modalities, The Virtual Hospital.
Hickey et al., Production of Enterolysin A by a Raw Milk Enterococcal Isolate Exhibiting Multiple Virulence Factors, Microbiology 149 (2003), 655-664.
Hirata et al., Pharmacokinetic Study of S-1, a Novel Oral Fluorouracil Antitumor Drug, Clinical Cancer Research vol. 5, 2000-2005, Aug. 1999.
Hoff et al., Phase I Study with Pharmacokinetics of S-1 on an Oral Daily Schedule for 28 Days in Patients with Solid Tumors, Clinical Cancer Research vol. 9, 134-142, Jan. 2003.
Hoffman et al., Pharmacodynamic and Pharmacokinetic Rationales for the Development of an Oral Controlled-Release Amoxicillin Dosage Form, Journal of Controlled Release 54 (1998) 29-37.
Hoffman et al., Influence of Macrolide Susceptibility on Efficacies of Clarithromycin and Azithromycin Against *Streptococcus pneumoniae* in a Murine Lung Infection Model, Antimicrobial Agents and Chemotherapy, Feb. 2003, p. 739-746, vol. 47, No. 2.
Hyde et al., Macrolide Resistance Among Invasive *Streptococcus pneumoniae* Isolates, JAMA. Oct. 17, 2001; 286(15):1857-62. (Abstract).
Iba et al., Comparison Between Continuous Intravenous and Oral Administration of 5-FU with LV, Gan to Kagaku Ryoho. Apr. 1999; 26(5):631-5 (Abstract).
Jacobs, Pharmacodynamic Approach to Antimicrobial Treatment for Respiratory Infections, Department of Pathology, Case Western Reserve University.
Kaplan et al., Macrolide Therapy of Group a *Streptococcal pharyngitis*: 10 Days of Macrolide Therapy (Clarithromycin) is More Effective in *Streptococcal* Eradication Than 5 Days (Azithromycin), Clin Infect Dis. Jun. 15, 2001;32(12):1798-802. Epub May 21, 2001. (Abstract).

(56) References Cited

OTHER PUBLICATIONS

Klugman, Bacteriological Evidence of Antibiotic Failure in Pneumococcal Lower Respiratory Tract Infections, Eur Respir J 2002; 20 Suppl. 36, 3s-8s.
Kramar et al., Statistical Optimisation of Diclofenac Sustained Release Pellets Coated with Polymethacrylic Films, Int J Pharm. Apr. 30, 2003;256(1-2):43-52. (Abstract).
Laine et al., Frequency and Clinical Outcome of Potentially Harmful Drug Metabolic Interactions in Patients Hospitalized on Internal and Pulmonary Medicine Wards: Focus on Warfarin and Cisapride, Therapeutic Drug Monitoring. 22(5):503-509, Oct. 2000. (Abstract).
Laine et al., Frequency and Clinical Outcome of Potentially Harmful Drug Metabolic Interactions in Patients Hospitalized on Internal and Pulmonary Medicine Wards: Focus on Warfarin and Cisapride, Therapeutic Drug Monitoring. 22(5):503-509, 2000.
Lamb et al., Ceftriaxone: An Update of its Use in the Management of Community-Acquired and Noscocomial Infections, Drugs. 2002;62(7):1041-89. (Abstract).
Lemer-Tung et al., Pharmacokinetics of Intrapericardial Administration of 5-Fluorouracil, Cancer Chemother Pharmacol. 1997;40(4):318-20. (Abstract).
Lin et al., Multiple-Dose Pharmacokinetics of Ceftibuten in Healthy Volunteers, Antimicrobial Agents and Chemotherapy, Feb. 1995, p. 356-358.
Lindsey et al., Extraction of Antibiotics From Agricultural Wastewater, USGS, 220th ACS Meeting Washington, D.C.; Aug. 20-24, 2000 (Abstract).
Livermore et al., Activity of Ertapenem Against Neisseria gonorrhoeae, Journal of Antimicrobial Chemotherapy 2004 54(1):280-281.
Lovmar et al., Kinetics of Macrolide Action, The Josamycin and Erythromycin Cases, J. Biol. Chem., vol. 279, Issue 51, 53506-53515, Dec. 17, 2004.
Mainz et al., Pharmacokinetics of Lansoprazole, Amoxicillin and Clarithromycin After Simultaneous and Single Administration, Journal of Antimicrobial Chemotherapy (2002) 50, 699-706.
Marten et al., Monthly Report, Jul. 2004, Pulsatile Dosing of Antifungal Compounds, UMBC; to Dr. Robert J. Guttendorf, Advancis Pharmaceutical Corp.
Marten et al., Monthly Report, Aug. 2004, Pulsatile Dosing of Antifungal Compounds, UMBC; to Dr. Robert J. Guttendorf, Advancis Pharmaceutical Corp.
Mazzei et al., How Macrolide Pharmacodynamics Affect Bacterial Killing, Infect Med 16(sE):22-28, 1999. (Abstract).
Nightingale, Pharmacokinetics and Pharmacodynamics of Newer Macrolides, Pediatric Infectious Disease Journal. 16(4):438-443, Apr. 1997. (Abstract).
Olofinlade et al. Anal Carcinoma: A 15-Year Retrospective Analysis, Scand J Gastroenterol 2000:35;1194-1199.
Pacifico et al., Comparative Efficacy and Safety of 3-Day Azithromycin and 10-Day Penicillin V Treatment of Group A Beta-Hemolytic Streptococcal pharyngitis in Children, Antimicroial Agents and Chemotherapy, Apr. 1996, 1005-1008, vol. 40, No. 4. (Abstract).
Parmar-Lapasia et al., A Comparison of Two Macrolide Antibiotics in the Treatment of Community-Acquired Infections, P & T (Pharmacy & Therapeutics), Oct. 2003, vol. 28, No. 10.
Peters et al., Fluorouracil (5FU) Pharmacokinetics in 5FU Prodrug Formulations with a Dihydropyrimidine Dehydrogenase Inhibitor, Journal of Clinical Oncology, vol. 19, Issue 22 Nov. 15, 2001: 4267-4269.
Polak, Pharmacokinetics of Amphotericin B and Flucytosine, Postgrad Med J. Sep. 1979;55(647):667-70.
Porter et al., Antibiotics and Infectious Diseases in Otolaryngology—HNS, Grand Rounds Presentation, UTMB, Dept. of Otolaryngology, May 8, 2002.
Ramminger et al., Transition-Metal Catalyzed Synthesis of Ketoprofen, J. Braz. Chem. Soc. vol. 11, No. 2, 105-111, 2000.

Ramu, Compounds and Methods that Reduce the Risk of Extravasation Injury Associated with the Use of Vesicant Antineoplastic Agents, Baylor College of Medicine, Aug. 6, 1998.
Ranga Rao et al., Influence of Molecular Size and Water Solubility of the Solute on its Release from Swelling and Erosion Controlled Polymeric Matrices, Journal of Controlled Release, 12 (1990) 133-141.
Reza et al., Comparative Evaluation of Plastic, Hydrophobic and Hydrophilic Polymers as Matrices for Controlled-Release Drug Delivery, J. Pharm Pharmaceut Sci, 6(2):282-291, 2003.
Richardson, The Discovery and Profile of Fluconazole, J Chemother. Feb. 1990;2(1):51-4 (Abstract) and Houang et al., Fluconazole Levels in Plasma and Vaginal Secretions of Patients After a 150-Milligram Single Oral Dose and Rate of Eradication of Infection in Vaginal Candidiasis, Antimicrob Agents Chemother. May 1990; 34(5):909-10 (Abstract).
Rivkees et al., Dexamethasone Treatment of Virilizing Congenital Adrenal Hyperplasia: The Ability to Achieve Normal Growth, Pediatrics 2000; 106; 767-773.
Roblin et al., In Vitro Activity of a New Ketolide Antibiotic, HMR 3647, Against Chlamydia pneumoniae, Antimicrob Agents Chemother. Jun. 1998; 42(6): 1515-1516.
Santini et al., The Potential of Amifostine: From Cytoprotectant to Therapeutic Agent, Haematologica Nov. 1999; 84(ii): 1035-1042.
Sanz et al., Cefepime Plus Amikacin Versus Piperacillin-Tazobactam Plus Amikacin for Initial Antibiotic Therapy in Hematology Patients with Febrile neutropenia: Results of an Open, Randomized, Multicentre Trial, Journal of Antimicrobial Chemotherapy (2002) 50, 79-88.
Schaad et al., Azithromycin Versus Penicillin V for Treatment of Acute Group A Streptococcal pharyngitis, The Pediatric Infectious Disease Journal: vol. 21(4) Apr. 2002 pp. 304-308.
Schweizer et al., "Single Shot" Prevention in Abdominal Surgery. Antibiotics with Long Half-Life (Cefriaxone, Omidazole) vs. Antibiotics with Short Half-Life (Cefazolin, Metronidazole, Clindamycin), Hely Chir Acta. Apr. 1994;60(4):483-8. (Abstract).
Shvartzman et al., Treatment of Streptococcal pharyngitis with Amoxycillin Once a Day, BMJ vol. 306, pp. 1170-1172, May 1, 1993.
Stringer et al., Section 3: Diseases of the Ear, Part 4: Inner Ear, Chapter 46: Ototoxicity, Paparella: vol. II, Otology and Neuro-Otology.
Suda et al., The Synthesis and In Vitro and In Vivo Stability of 5-Fluorouracil Prodrugs Which Possess Serum Albumin binding Potency, Biol Pharm Bull. Sep. 1993;16(9):876-8. (Abstract).
Sandip et al., Controlled Release Formulation of Tramadol Hydrochloride Using Hydrophilic and Hydrophobic Matrix System, AAPS PharmSciTech 2003; 4 (3) Article 31.
Todar's Online Textbook of Bacteriology, Antimicrobial Agents Used in Treatment of Infectious Disease, 2002 Kenneth Todar University of Wisconsin-Madison Department of Bacteriology.
Vanderkooi et al., Antimicrobial Resistance and the Pneumococcus, Infectious Diseases and Microbiology, vol. 3, Issue 5, May 2004.
Villalobos et al., Pharmacokinetics and Pharmacodynamics of Antibacterial Agents in Pediatrics: A Practical Approach, Jacksonville Medicine, Aug. 1998.
Waters, Colorectal Cancer-Drug Treatment, Hospital Pharmacist, vol. 11, pp. 179-192, May 2004.
Wattenberg, Prevention of Carcinogenesis of the Respiratory Tract by Chemopreventive Agents Delivered by Aerosol, International Society of Cancer Chemoprevention, vol. 1, No. 5, Jan. 2003.
Whitehead et al., Amoxycillin Release From a Floating Dosage Form Based on Alginates, International Journal of Pharmaceutics 210 (2000) 45-49.
Yousef et al., Combined Action of Amoxycillin and Dicloxacillin Against Staphylococcus aureus in Vitro, Pharmazie Sep. 1985; 40(9):650-1. (Abstract).
About Macrolides, About That Bug.com.
Acepromazine Maleate, Drugs.
Allergy Site Navigator, Drug Classification A-D.
Amoxycillin (As Trihydrate), Moxyvit.
Amoxicillin + Clavulanate, PetPlace.com.
Answers.com, Macrolide.
Antimetabolites, GPnotebook.

(56) References Cited

OTHER PUBLICATIONS

Augmentin, Product Information, GlaxoSmithKline, Physicians Desk References, pp. 1421-1433.
Augmentin XR (PDR entry for) (GlaxoSmithKline), (Amoxicillin/ Clavulanate Potassium), Extended Release Tablets, Jun. 2004.
Beta Lactam Antibiotics, Health 24.com.
Biaxin XL, Once-Daily Biaxin XL Clarithromycin Extended-Release Tablets, Abbott Laboratories Online.
Biaxin XL, Once-daily, Abbott.
Biaxin, Dosage and Administration.
Biaxin Filmtab, Biaxin XL Filmtab, Biaxin Granules, pp. 1-25, Abbott Laboratories.
Body Chemistry, Acid Alkaline Foods, Acid Reflux? Gas, Acid Indigestion, Acid/Alkaline Balance.
Carers of Crohns, Antibiotics.
Citizen Petition, McNeil Consumer & Specialty Pharmaceuticals, Mar. 19, 2004.
Clarithromycin Extended-Release Scientific Posters Presented to the 39th Interscience Conference on Antimicrobial Agents and Chemotherapy (ICAAC), San Francisco, Sep. 26-29, 1999.
Clearance and the Elimination Rate Constant, Ke (Elimination Rate)—Half-Life, Oct. 14, 2002.
Complementary Medicine Saves Money, Medicine, Greenhealthwatch.com.
Cross-Reference Art Collections, 901-907; USPTO.gov.
Declaration of Michael J. Rybak. from the prosecution history of U.S. Appl. No. 09/792,092; Sep. 23, 2002.
Dispensing Errors With Depakote, New Formulation Creates Confusion, Patient Safety, Practitioners Reporting News, USP Issued Mar. 3, 2001.
Drugs.com, Drug Information for Diclofenac (Topical).
Drug, Bio-Affecting and Body Treating Compositions (Class 424), 475 Sustained or differential release, United States Patent and Trademark Office.
Elimination Rate Constant/Half-Life, Ke (Elimination Rate)—Half-Life, Oct. 14, 2002.
Emulsions.
Encyclopedia Britannica Online, Types of Drugs>Antimicrobial Drugs>Antibiotics>Macrolides.
Excenel, Swine Health Management, Prewean Program. Pfizer Salud Animal.
Fabrication of Metronidazole Strips, 996 Die Pharmazie 50(Feb. 1995) No. 2.
Five vs. 10 Days of Therapy for *Streptococcal pharyngitis*, American Family Physician, Feb. 15, 2001.
Food and Drug Administration Center for Drug Evaluation and Research Approved Drug Products With Therapetutic Equivalence Evaluations, 24th Edition.
Getting a Drug Into the Body: Absorption.
Highlights on Antineoplastic Drugs, Pharmacia, vol. 11. No. 4, 1993.
Jock Itch and Other dermatophytes . . . , Mycolog.
Klarithran, Ranbaxy(SA)(PTY) Ltd, Jun. 2005.
Klucel Hydroxypropylcellulose (HPC). Hercules Incorporated.
MedicineNet.com, Generic Name: Acyclovir, Brand Name: Zovirax, Dec. 31, 1997.
Meeting the Challenge of a New Generation of Respiratory Pathogens, MAC.
The Merck Index, An Encyclopedia of Chemicals, Drugs, and Biologicals, Twelfth Edition, pp. 397-398.
Methods of Formulating Controlled Release Products Outside of the Claims of Forest Laboratory Patents U.S. 4,369,172 and U.S. 4,389,393, Technical Information, Dow Chemical, Feb. 1991.
Miconazole, The Merck Index Results-Form View, Monograph No. 06202.
Mode of Action of Macrolides in Blocking Translation During Bacterial Protein Synthesis: Blocking Peptidyltransferase. Doc Kaiser's Microbiology Home Page, Oct. 13, 2004.
Module 8—Therapeutics. May 2, 2002, Newcastle., BPAIIG Immunology/Infectious Diseases Training Programme, Module: Therapeutics.
Monistat, Which Treatment is Right for You?, Vaginal vs. Oral Therapy.
Neisseria Meningitidis, The Doctor's Doctor, Nov. 8, 2004.
New-Generation Aromatase Inhibitor for Breast Cancer: Anastrozole Challenges Tamoxifen in First-Line Therapy, 10th European Cancer Conference (ECCO 10), Vienna, Austria/ Sep. 12-16, 1999.
New Product Newswire, Drug Topics Archive, Aug. 5, 2002.
Nitrofurantoin, Eckerd Prescription Advisor, Feb. 15, 2001.
Nursing, Cancer Nursing: Principles and Practice, Fifth Edition, Jones and Bartlett Publishers, 2000.
Oral Capecitabine Should Improve Convenience of Chemoradiation for Locally Advanced Rectal Cancer-New Treatment Appears to be Safe and Effective, PeerView Press, Chemotherapy (ICAAC), Sep. 27-30, 2002; San Diego, CA., 40th Annual Meeting of Infectious Diseases Society.
Oral Extended (Controlled) Release Dosage Forms, In Vivo Bioequivalence and In Vitro Dissolution Testing, Office of Generic Drugs.
Pharmaceuticals, Pharmacos Unit F2 Pharmaceuticals V 6.0, Eudralex Collection 3AQ19a 1992.
Physicians Desk Reference, PDR 57 Edition 2003, p. 402/Abbott.
Principles of Diagnosis of Infectious Diseases and Antimicrobial Therapy, Chapter 1.
Procardia XL (Nifedipine) Extended Release Tablets for Oral Use, 69-4467-00-8, Pfizer Labs, Aug. 2003.
Summary of Product Characteristics, Doxycycline Capsules BP 50mg.
Sustained or Differential Release Type, USPTO Classification Definitions (Dec. 2002 Edition) 964.
Sustained-Release Dosage Forms, Degussa, Rohm Pharma Polymers.
Testicular Cancer. Questions and Answers, Cancer Facts, National Cancer Institute, Aug. 14, 2003.
Traditional Chemotherapy, Chapter 25 from Prevention and Therapy of Cancer and Other Common Disease: Alternative and Traditional Approaches; Infomedix 1996.
Bahnmuller, Metabolites of Microorganisms. 248. Synthetic Analogs of Saphenamycin, J. Antibiot (Tokyo). Nov. 1988; 41(11): 1552-60.
Borman, Chemistry Highlights 2005, Chemical & Engineering News, Dec. 19, 2005, vol. 83, No. 51, pp. 15-20.
Cirz et al., Inhibition of Mutation and Combating the Evolution of Antibiotic Resistance, PLOS Biology, Jun. 2005, vol. 3, Issue 6,e176, pp. 1024-1033.
Darst, New Inhibitors Targeting Bacterial RNA Polymerase, Trends in Biochemical Sciences, vol. 29, No. 4, Apr. 2004, pp. 159-162.
Dellit, M.D., Tim, University of Washington and Infectious Diseases Society of Washington; Jeffrey Duchin, MD, Public Health-Seattle & King County and University of Washington; Jo Hofmann, MD, Washington State Department of Health and University of Washington; Erika Gurmai Olson, MD, Tacoma-Pierce County Health Department Antibiotic Resistance Task Force, Interim Guidelines for Evaluation and Management of Community-Associated Methicillin-Resistant *Staphylococcus aureus* Skin and Soft Tissue Infections in Outpatient Settings, Sep. 2, 2004.
Geiger et al., Metabolites of Microorganisms. 247. Phenazines from *Streptomyces antibioticus*, Strain Tu 2706, J Antibiot (Tokyo). Nov. 1988;41 (11): 1542-51.
Gorwitz et al., Strategies for Clinical Management of MRSA in the Community: Summary of an Experts' Meeting Convened by the Centers for Disease Control and Prevention, Department of Health and Human Services Centers for Disease Control and Prevention, Mar. 2006.
Henry, Disabling Resistance Inhibiting Key Protease Prevents Bacteria From Evolving Drug Resistance, Chemical and Engineering News, May 16, 2005, vol. 83, No. 20, p. 8.
Johnson, N.J. Experts Urge Prudent Antibiotic Use, Examiner.Com, The Associated Press, Jul. 31, 2006.
Kitahara et al., Saphenamycin, A Novel Antibiotic From a Strain of *Streptomyces*, J Antibiot (Tokyo). Oct. 1982; 35(10):1412-4.
Laursen et al., Solid-Phase Synthesis of New Saphenamycin Analogues with Antimicrobial Activity, Bioorg. Med. Chem. Lett. Jan. 21, 2002; 12(2):171-5.

(56) References Cited

OTHER PUBLICATIONS

Laursen et al., First Synthesis of Racemic Saphenamycin and Its Enantiomers. Investigation of Biological Activity, Bioorg. Med. Chem. Mar. 6, 2003;11(5):723-31.

Laursen et aL, Efficient Synthesis of Glycosylated Phenazine Natural Products and Analogs with DISAL (Methyl 3, 5-Dinitrosalicylate) Glycosyl Donors, Org. Biomol. Chem. Sep. 21, 2003;1(18):3147-53.

Reusser, Inhibition of Ribosomal and RNA Polymerase Functions by Rubradirin and Its Aglycone, J Antibiot (Tokyo). Nov. 1979;32(11):1186-92.

Rihn, et al., Community-Acquired Methicillin-Resistant *Staphylococcus aureus*: An Emerging Problem in the Athletic Population, Am J Sports Med. Dec. 2005;33(12): 1924-9.

Salmenlinna et al., Community-Acquired Methicillin-Resistant *Staphylococcus aureus*, Finland, Emerg. Infect. Dis. Jun. 2002;8(6):602-7.

Salmenlinna et al., Community-Acquired Methicillin-Resistant *Staphylococcus aureus*, Finland, Emerging Infectious Diseases, vol. 8, No. 6, Jun. 2002, pp. 602-607.

Vandenesch et al., Community-Acquired Methicillin-Resistant *Staphylococcus aureus* Carrying Panton-Valentine Leukocidin Genes: Worldwide Emergence, Emerg. Infect. Dis. Aug. 2003;9(8):978-84.

Can We Prevent Bacteria From Developing Resistance to Antibiotics?, Sep. 2005, AAPS News Magazine 15.

Healthcare-Associated Methicillin Resistant *Staphylococcus aureus* (HA-MRSA), Department of Health and Human Services, Centers for Disease Control and Prevention, Jun. 1, 2005.

Methicillin-Resistant *Staphylococcus aureus*, HealthLink, Medical College of Wisconsin, Information Provided by the Wisconsin Department of Health and Family Services, Article Reviewed: Apr. 10, 2000, 2003 Medical College of Wisconsin.

Methicillin-Resistant *Staphylococcus aureus* (MRSA) Infection, Written by Dr. Alan Johnson, Clinical Scientist, Website: www.mrsasupport.co.uk, Aug. 1, 2005.

The Public's Health, Back-To-School: Review Immunization Records Early, What Doctors and Parents Need to Know About Immunizations and School, vol. 5, No. 7, Jul.-Aug. 2005.

Sulfonamide Class Antibiotics, ChemicalLand21.com.

* cited by examiner

ROBUST PELLET

This application claims the priority of U.S. Provisional Application Ser. No. 60/494,155 filed on Aug. 11, 2003, the disclosures of which are hereby incorporated by reference in their entireties.

The present invention relates to an oral dosage form comprising robust pellets that contain, percentage-wise, a high dosage of an active drug agent, and which also contain additional components that enhance the absorption and solubility of the active drug agent within the gastrointestinal tract (GI tract), without diminishing the robust nature of the pellets. As used herein and as known in the art, the term "robust pellet" means a pellet capable of retaining its physical integrity during and after processing into a dosage form, and after undergoing standard coating procedures. The robust pellets of the present invention permit the dosage form to be effectively compounded to produce a finished pharmaceutical product.

INTRODUCTION

It is well known in the art that drugs that are solubilized in the GI tract are more easily absorbed. Yet, one of the biggest challenges in formulation and product development of pharmaceuticals is that of insuring and controlling the solubility and the absorbability of the final product within the human GI tract. One of the ways to meet this challenge is to use absorption-enhancing agents like Labrasol, Cremophor, PEG, and Polysorbates, or solubility-enhancing agents such as Pharmasolve and Transcutol-P. Frequently, however, the amount of enhancers required for a targeted GI tract delivery in a formulation is beyond the feasible amount for processing solid oral dosage forms. These cumbersome enhancer amounts often result in less than robust pellets that may be too brittle, sticky, or light, thus robbing the pellets of essential utilities that may be necessary for efficient downstream processing. Many times the formulator's only option is to reduce the total amount of these enhancers so that the formulation can be processed.

Liquid oral absorption enhancers have been traditionally included in pharmaceutical formulations by filling the enhancers and the active agents into hard or soft gelatin capsules. These formulations require no further processing as they readily provide oral dosage forms that can be effectively administered to a patient. Numerous examples of delivery systems of this nature are available in the prior art. See U.S. Pat. Nos. 6,267,985; 4,388,307; 4,572,915; and 4,713,246. An example of a marketed product of this kind is Neoral, which contains cyclosporin and a mixture of liquid absorption enhancers.

Unfortunately, some specific types of dosage forms do not lend themselves to traditional gelatin capsule delivery, such as dosage forms that contain drugs that are sensitive to stomach acid. The gelatin capsule methods are also ineffective in formulations that contemplate a modified release pattern of active drug agent delivery. Traditional liquid filled gelatin capsule delivery systems are typically designed to keep insoluble and/or less permeable active agents in a solubilized and/or emulsified state so that when the dosage form is introduced into the stomach the active agent will be readily absorbed. The use of the gelatin capsule systems therefore presents serious challenges to the formulator, who needs to prevent an acid sensitive active agent from coming into contact with stomach acid so as not to modify his intended release pattern.

Another difficulty in using hard or soft gelatin capsules for the application of the present invention is that the hard or soft gelatin capsules are difficult to process further. For example it is not customary to cover a gelatin capsule with an enteric polymer for site specific delivery since gelatin ideally dissolves at the pH of the stomach and would not readily dissolve at the pH of the small intestine.

In addition, utilizing a hard or soft gelatin capsule containing high volumes of a liquid absorption enhancer, would not provide a means by which the absorption enhancer could travel through the GI tract with the active ingredient. Without the absorption enhancer and the active ingredient arriving at the site of absorption within a reasonably short period of each other, the absorption enhancer would not be beneficial. In a gelatin capsule system, the essential absorption enhancer would get washed away in the stomach if the delivery system dissolved there.

The robust pellets of the present invention are particularly useful in modified release formulations, such as those formulations comprising matrix tablets. In addition, the Pulsys™ dosage form, another type of modified release technology, among others not specifically named here, would benefit from the present invention. The Pulsys™ dosage form is a pulsatile delivery system, which provides an oral drug product that releases an active drug agent at numerous sites along the GI tract, in pulses over the course of 12 hours or less. The Pulsys™ system is particularly useful in delivering an entire day's dosage of a drug by way of once-a-day administration; its parameters are illustrated by U.S. Pat. Nos. 6,565,882; 6,544,555; and 6,541,014; issued to Rudnic et al., the disclosures of each of which are hereby incorporated by reference in their entireties.

In order to target specific sites along the GI tract, it is often necessary to apply various functional coatings to the dosage form. These coatings may be pH dependent, pH independent, environmentally dependent, or triggered by other mechanisms necessary to achieve the desired GI tract delivery. Before such coatings can be applied, however, it is often necessary that the pellet be subjected to any number of downstream processes such as extrusion, spheronization, roller compaction, compression, fluid-bed drying, wet granulation, and tabletting. While the above mentioned absorption enhancers and solubilizing agents are well known in the formulation arts, the formulator's inclusion of these materials usually makes it very difficult to achieve a high dosage active ingredient bead, or pellet, that can withstand the further processing necessary to allow application of the desired functional coatings. The robust pellets of present invention make it possible to deliver a high dose of active drug agent to specific sites along the GI tract by uniquely combining absorbance enhancing surfactants, with solubilizing agents that act as a solvent for the active drug agent. High dosage formulations that utilize surfactant-type absorption enhancers of the present invention tend to result in pellets that are soft and tacky. Additionally, most solid pellet formulations eschew the present invention's use of solvents for the active drug component, because the use of solvents tends to result in pellets that are too brittle, causing the pellet to fall apart.

The present invention combines a high dosage of an active drug ingredient with a surfactant-type absorption enhancer, and with a solubilizing agent that is a solvent for the active drug component. This combination surprisingly and counter-intuitively results in a less brittle pellet that can withstand the physical stresses of downstream pharmaceutical processing. Given the tendency for solvent additions to result in a more brittle pellet, one of ordinary skill in the art would have not have expected that the present invention's combination of a solvent with a surfactant would result in pellets that were more robust and less brittle. The surfactant and solvent combination of the present invention also prevents the pellets from being too sticky.

Pellets, beads, and granules that are ideal for such downstream processing as drying, extrusion, spheronization, roller compaction, coating and compression should, in general, be moderately malleable, flexible, and dense. Pellets, beads, and granules that are too brittle, sticky, or light (low density) may sustain significant physical damage during the downstream processes mentioned above. These physical damages directly correlate to poor process efficiency and lower overall product yields. When used in formulations many of the absorption enhancers or solubilizing agents result in pellets having the above-mentioned undesirable characteristics. These undesirable characteristics lead to processing failures, making it difficult to manufacture products such as tablets or those that would utilize the Pulsys™ delivery system. For example, Labrasol, Cremophor El, and other like compounds can be used as absorption-enhancing agents for beta-lactam antibiotics. However, when the absorption-enhancing agents are present in higher concentrations (greater than 5%), the formulations will not process well due to the oily natures of Labrasol, Cremophor El, and other like compounds. These formulations tend to be soft and tacky. Similarly, Pharmasolve, Transcutol, pharmaceutically accepted alcohols, pharmaceutically accepted hydrocarbons, and their derivatives can be used as solubility-enhancing agents for beta-lactam antibiotics. However, when the solubility-enhancing agents are present in higher concentrations (greater than 5%), the formulations will not process well owing to the brittleness of the wetted granules, caused by Pharmasolve, Transcutol, pharmaceutically accepted alcohols, pharmaceutically accepted hydrocarbons, and their derivatives.

While Labrasol, Cremophor El, and other like compounds form very soft and tacky granules when processed with beta-lactam antibiotics, and Pharmasolve, Transcutol, pharmaceutically accepted alcohols, pharmaceutically accepted hydrocarbons, and their derivatives form very brittle granules when processed with beta-lactam antibiotics, the present invention exhibits an unexpected result in that combining both of these enhancing agents within the same formulation leads to more robust formulation pellets or granules. These pellets or granules make downstream processing such as fluid-bed drying, coating, and spheronization, both possible, and more efficient, by increasing the total product yield.

Similarly, within the scope of the present invention Pharmasolve, Transcutol, pharmaceutically accepted alcohol, pharmaceutically accepted hydrocarbons and their derivatives can be used in formulations with many other absorption-enhancing agents that would otherwise result in pellets and granules that tend to be too oily or too waxy. Non-limiting examples of such other absorption-enhancing agents would include Cremophor EL, Gelucire, PEG, Triglycerides, Fatty Acids, Non-ionic Surfactants, Ionic Surfactants, Hydrophobic and Hydrophilic Surfactants, and Polysorbates and Polysorbate formulations.

SUMMARY OF THE INVENTION

The present invention is directed to a robust pellet containing high dosage amounts of an active drug agent, while also containing both a pharmaceutically acceptable absorption enhancing surfactant, and a pharmaceutically acceptable solubilizing agent as a solvent for the drug component. As used herein the term high dosage means that the drug component comprises at least 50% by weight (W/W) of the robust pellet. The present invention is also directed to a method of making a robust pellet, and further directed to the robust pellet made by that method. The present invention is also directed to a pharmaceutical dosage form comprising robust pellets, which dosage form can withstand further processing into a finished pharmaceutical product having modified release characteristics, such as those embodied in the Pulsys™ system. The present invention is also directed to a finished pharmaceutical product comprising dosage forms that are comprised of the hereinabove and hereinbelow described robust pellets.

The pharmaceutically acceptable absorption enhancers that are useful in the present invention are those of the surfactant type, spanning the range of hydrophyllic/lipophyllic balances, HLB's, such as, for example, medium and long chain triglycerides. The triglycerides can be selected from the group consisting of almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; soy oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; glyceryl tricaprylate/caprate/stearate; saturated polyglycolized glycerides; linoleic glycerides; caprylic/capric glycerides; modified triglycerides; fractionated triglycerides; and mixtures thereof.

The pharmaceutically acceptable solubility enhancers that are useful in the present invention are of the polar and non-polar solvent types, such as N-Methyl pyrolidone (NMP), transcutol, ethanol, isopropyl alcohol, ether, and pharmaceutically accepted hydrocarbons and their derivatives.

In a preferred embodiment, the active drug agent is an anti-infective agent. In a more preferred embodiment, the active drug agent is an antibiotic. In a still more preferred embodiment, the active drug agent is a beta lactam antibiotic.

In a particularly preferred embodiment the robust pellets of the present invention comprise 70-90% Amoxicillin, 2-10% Labrasol, and 2-10% N-Methyl pyrolidine. In a similarly particularly preferred embodiment the dosage forms of the present invention are comprised of robust pellets comprising 70-90% Amoxicillin, 2-10% Labrasol, and 2-10% N-Methyl pyrolidine. In yet another particularly preferred embodiment the finished pharmaceutical products of the present invention are comprised of dosage forms that are comprised of robust pellets comprising 70-90% Amoxicillin, 2-10% Labrasol, and 2-10% N-Methyl pyrolidine.

Specific Ingredients

The present invention may be used to produce robust pellets and finished pharmaceutical products containing any drug. However, non-limiting examples of the active drug agents useful as the active ingredients in the present invention include the beta-lactam penicillins, such as Amoxicillin, Penicillin, and Dicloxicillin; the cephalosporin antibiotics, such as Cefixime and Cefpodoxime proxetil; the macrolides, such as Clarithromycin and Erythromycin; the tetracyclines such as tetracycline, doxycycline, chlortetracycline, and minocycline; the Fluoroquinolones, such as Ciprofloxacin and Norfloxacin; and the Sulfonamides, such as Sulfadiazine and Sulfisoxazole.

Non-limiting examples of the absorption enhancing agents useful in the present invention include non-ionic surfactants (including alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; sugar esters, sugar ethers; sucroglycerides; and mixtures thereof); hydrophilic surfactants (including PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, a poloxamer, and mixtures thereof), hydrophobic surfactants, short and long chain fatty acids/triglycerides, propylene glycol esters, glycerol esters, polyglycerol esters, mono and diesters, alkoxylates (Cremophor EL), and Caprylocaproyl Macrogogol-6 Glycerides (Labrasol).

Non-limiting examples of the solubility enhancing agents useful in the present invention include Methyl-2 Pyrrolidone (Pharmasolve), diethylene glycol monoethyl ether (Transcutol P), pharmaceutically accepted alcohol (isopropyl alcohol and methanol), and pharmaceutically accepted hydrocarbons and any derivative of the above mentioned.

Other inactive ingredients may include but are not limited to microcrystalline cellulose, lactose, dextrose, starch, hydroxymethylcellulose, polyvinal pyrolidon, methacrylic acid copolymers, ethyl cellulose, HPMC acetate succinate, cellulose acetate phthalate, triethyl citrate, talc, sodium lauryl sulfate, and other pharmaceutically acceptable carriers.

Use of the robust pellets of the present invention in pharmaceutical dosage form production and finished pharmaceutical product production results in improved efficiencies and effectiveness in downstream processing operations. Non-limiting examples of such processing operations include wet granulation, fluid bed drying, extrusion, spheronization, fluid bed coating, roller compaction, and tablet coating.

In addition to the above description, the following Examples are provided to further enable the artisan of ordinary skill to practice the best mode of the present invention.

EXAMPLE 1

Immediate Release Pellets

The term W/W as used herein is representative of a weight to weight ratio of the material specified to the weight of the unit dosage form as a whole.

| Name of Ingredient | % W/W |
| --- | --- |
| Amoxicillin Trihydrate | 80% |
| Microcrystalline Cellulose | 14% |
| Labrasol | 2% |
| Pharmasolve | 2% |
| PVP K30 | 2% |
| Water | As needed |

EXAMPLE 2

Immediate Release Pellets

| Name of Ingredient | % W/W |
| --- | --- |
| Amoxicillin Trihydrate | 80% |
| Labrasol | 10% |
| Pharmasolve | 6% |
| PVP K30 | 4% |
| Water | As needed |

Preparation of Immediate Release Pellets

Labrasol, Pharmasolve, and PVPK30 are dissolved in a predetermined amount of water. The solution is added to a premixed blend of Amoxicillin Trihydrate and microcrystalline cellulose in a low or high shear granulator. The wet mass is then fed through an extruder to form dense elongated strands. These strands are then rounded in a spheronizer. The resultant pellets are then dried with a fluid bed drier. At this point, the pellets of desired size are collected using sieves.

EXAMPLE 3

Immediate Release Granules

| Name of Ingredient | % W/W |
| --- | --- |
| Clarithromycin | 94% |
| Cremophor EL | 2% |
| Transcutol P | 2% |
| PVP K30 | 2% |
| Water | As needed |

EXAMPLE 4

Immediate Release Granules

| Name of Ingredient | % W/W |
| --- | --- |
| Clarithromycin | 77% |
| Microcrystalline Cellulose | 11% |
| Cremophor EL | 5% |
| Transcutol P | 5% |
| Hydroxypropylmethylcellulose | 2% |
| Water | As needed |

EXAMPLE 5

Immediate Release Granules

| Name of Ingredient | % W/W |
| --- | --- |
| Clarithromycin | 77% |
| Cremophor EL | 10% |
| Transcutol P | 10% |
| Hydroxypropylmethylcellulose | 3% |
| Water | As needed |

Preparation of Immediate Release Granules

Cremophor EL, Transcutol P, and HPMC are dissolved in a predetermined amount of water. The solution is added to a premixed blend of Amoxicillin Trihydrate and microcrystalline cellulose in a low or high shear granulator. The granules are milled to desired size and then dried with a fluid bed drier. At this point, the granules of desired size are collected using sieves.

EXAMPLE 6

Enteric Coated Pellets

| Name of Ingredient | % W/W |
| --- | --- |
| Clarithromycin | 77% |
| Acconon E | 10% |
| Transcutol P | 5% |
| Lactose Monohydrate | 6% |
| PVP K30 | 2% |
| Water | As needed |

Enteric Coating System: Methyacrylic Copolymer (Eudragit L30D-55)

| Name of Ingredient | % W/W |
| --- | --- |
| Methacrylic Copolymer (Eudragit L30D-55) | 53% |
| Talc | 2% |
| Triethyl Citrate | 8% |
| Water | 38% |

Preparation of Enteric Coated Pellets

Acconon E, Transcutol P, and PVPK30 are dissolved in a predetermined amount of water. The solution is added to a premixed blend of Amoxicillin Trihydrate and lactose monohydrate in a low or high shear granulator. The wet mass is then fed through an extruder to form dense elongated strands. These strands are then rounded in a spheronizer. The pellets are then dried with a fluid bed drier. At this point, the pellets of desired sizes are collected using sieves.

The enteric coating system is prepared by mixing the talc, triethyl citrate, and water together for 30 minutes and then adding to the methacrylic copolymer dispersion, and then further mixing for an additional 30 minutes. The immediate release pellets are coated in a fluid bed bottom spray coater. The inlet air temperature should be adjusted to maintain a product temperature of 25-30° C. A 10-30% weight gain based on solids can be applied to generate a consistent film coat that will provide adequate acid protection.

EXAMPLE 7

Sustained Release Coated Pellets

Immediate Release Pellets

| Name of Ingredient | % W/W |
| --- | --- |
| Amoxicillin Trihydrate | 80% |
| Labrafil CS | 10% |
| Pharmasolve | 5% |
| Microcrystalline Cellulose | 6% |
| Hydroxymethylcellulose | 2% |
| Water | As needed |

Sustain Release Coating System: Ethyl Cellulose (Aquacoat ECD)

| Name of Ingredient | % W/W |
| --- | --- |
| Ethyl Cellulose Dispersion | 38% |
| Dibutyl Sebbacate | 3% |
| Water | 60% |

Preparation of Sustained Release Coated Pellets

Labrafil CS, Pharmasolve, and HPMC are dissolved in a predetermined amount of water. The solution is added to a premixed blend of Amoxicillin Trihydrate and microcrystalline cellulose in a low or high shear granulator. The wet mass is then fed through an extruder to form dense elongated strands. These strands are then rounded in a spheronizer. The pellets are then dried with a fluid bed drier. At this point, the pellets of desired sizes are collected using sieves.

The sustained release coating system is prepared by mixing the ethyl cellulose dispersion and dibutyl sebbacate for 30 minutes. The inlet air temperature should be adjusted to maintain a product temperature of 30° C.-40° C. A 5-20% weight gain based on solids can be applied. The weight gain level will depend on the desired in-vitro release profile.

EXAMPLE 8

High Drug Load Immediate Release Granules or Pellets

| Name of Ingredient | % W/W |
| --- | --- |
| Amoxicillin Trihydrate | 90% |
| Cremophor EL | 5% |
| Pharmasolve | 2% |
| PVP K30 | 3% |
| Water | As needed |

Preparation of High Drug Load Immediate Release Granules or Pellets

Cremophor EL, Pharmaslve, and PVP K30 are dissolved in a predetermined amount of water. The solution is added to Amoxicillin Trihydrate in a low or high shear granulator. The granules are milled or extruded/spheronized to desired size and then dried with a fluid bed drier. At this point, the granules/pellet of desired size are collected using sieves.

EXAMPLE 9

Low Drug Load Immediate Release Granules or Pellets

| Name of Ingredient | % W/W |
|---|---|
| Amoxicillin Trihydrate | 51% |
| Cremophor EL | 15% |
| Pharmasolve | 10% |
| PVP K30 | 4% |
| Water | As needed |

Preparation of Low Drug Load Immediate Release Granules or Pellets

Cremophor EL, Pharmaslve, and PVP K30 are dissolved in a predetermined amount of water. The solution is added to Amoxicillin Trihydrate in a low or high shear granulator. The granules are milled or extruded/spheronized to desired size and then dried with a fluid bed drier. At this point, the granules/pellet of desired size are collected using sieves.

We claim:

1. A pharmaceutical pellet comprising a granulated mixture, wherein the granulated mixture comprises at least one active ingredient drug component, at least one pharmaceutically acceptable absorption enhancing agent, wherein said at least one pharmaceutically acceptable absorption enhancing agent is selected from the group consisting of: non ionic surfactants, hydrophilic surfactants, hydrophobic surfactants, short chain fatty acids, long chain fatty acids, short chain triglycerides, and long chain triglycerides, and at least one pharmaceutically acceptable solubility enhancing agent, wherein said at least one pharmaceutically acceptable solubility enhancing agent is selected from the group consisting of: Methyl-2 Pyrrolidone, diethylene glycol monoethyl ether, and pharmaceutically accepted alcohols; wherein said at least one active ingredient drug component comprises at least one beta lactam penicillin and constitutes at least 50% W/W of said pharmaceutical pellet, wherein said at least one pharmaceutically acceptable absorption enhancing agent constitutes 2 to 10% W/W of said pharmaceutical pellet; wherein said at least one pharmaceutically acceptable solubility enhancing agent is a solvent for said at least one active ingredient drug component.

2. The pharmaceutical pellet of claim 1, wherein said at least one active ingredient drag component is Amoxicillin present in an amount of from 70-90% W/W of said pharmaceutical pellet, wherein said at least one pharmaceutically acceptable absorption enhancing agent is Caprylocaproyl Macrogogol-6 Glycerides present in an amount of from 2-10% W/W of said pharmaceutical pellet, and wherein said at least one pharmaceutically acceptable solubility enhancing agent is Methyl-2 Pyrrolidone present in an amount of 2-10% W/W of said pharmaceutical pellet.

3. The pharmaceutical pellet of claim 1, wherein said active drug component is Amoxicillin.

4. The pharmaceutical pellet of claim 1, wherein said Beta-Lactam Penicillin is selected from the group consisting of Amoxicillin, Penicillin, and Dicloxicillin.

5. A pharmaceutical pellet comprising a granulated mixture, wherein the granulated mixture comprises: at least one active ingredient drug component comprising at least one beta lactam penicillin, at least one pharmaceutically acceptable absorption enhancing agent, and at least one pharmaceutically acceptable solubility enhancing agent, wherein said at least one pharmaceutical acceptable solubility enhancing agent is selected from the group consist of: Methyl-2 Pyrrolidone, diethylene glycol monoethyl ether, and pharmaceutically accepted alcohols; wherein said at least one active ingredient drug component constitutes at least 50% W/W of said pharmaceutical pellet, wherein said at least one pharmaceutically acceptable absorption enhancing agent is a surfactant triglyceride; wherein said at least one pharmaceutically acceptable solubility enhancing agent is a solvent for said at least one active ingredient drug component; wherein said at least one pharmaceutically acceptable absorption enhancing agent constitutes 2 to 10% W/W of said pharmaceutical pellet; wherein said at least one pharmaceutically acceptable solubility enhancing agent constitutes 2 to 10% W/W of said pharmaceutical pellet.

6. The pharmaceutical pellet of claim 5, wherein the triglyceride is a caprylic/capric glyceride.

7. The pharmaceutical pellet of claim 5, wherein said beta-lactam penicillin is selected from the group consisting of Amoxicillin, Penicillin, and Dicloxicillin.

8. The pharmaceutical pellet of claim 7, wherein said beta-lactam penicillin is Amoxicillin and is present in an amount of from 70-90% W/W of said pharmaceutical pellet.

9. The pharmaceutical pellet of claim 5, wherein said at least one pharmaceutically acceptable solubility enhancing agent is Methyl-2 Pyrrolidone or diethylene glycol monoethyl ether and said beta-lactam penicillin is Amoxicillin and said Amoxicillin is present in an amount of from 70-90% W/W of said pharmaceutical pellet.

10. The pharmaceutical pellet of claim 1, wherein said at least one pharmaceutically acceptable solubility enhancing agent constitutes 2 to 10% W/W of said pharmaceutical pellet.

11. The pharmaceutical pellet of claim 10, wherein said at least one pharmaceutically acceptable solubility enhancing agent is Methyl-2 Pyrrolidone or diethylene glycol monoethyl ether and said at least one pharmaceutically acceptable absorption enhancing agent is an alkoxylate or a caprylocaproyl macrogogol-6 glyceride.

12. The pharmaceutical pellet of claim 11, wherein said beta-lactam penicillin is selected from the group consisting of Amoxicillin, Penicillin, and Dicloxicillin.

13. The pharmaceutical pellet of claim 12, wherein said beta lactam penicillin is Amoxicillin and is present in an amount of from 70-90% W/W of said pharmaceutical pellet.

14. The pharmaceutical pellet of claim 13, wherein said at least one pharmaceutically acceptable solubility enhancing agent is Methyl-2 Pyrrolidone and said at least one pharmaceutically acceptable absorption enhancing agent is caprylocaproyl macrogogol-6 glyceride.

15. The pharmaceutical pellet of claim 10, wherein said beta-lactam penicillin is Amoxicillin.

16. The pharmaceutical pellet of claim 5, wherein said beta-lactam penicillin is Amoxicillin.

* * * * *

UNITED STATES PATENT AND TRADEMARK OFFICE
CERTIFICATE OF CORRECTION

| | | |
|---|---|---|
| PATENT NO. | : 8,758,820 B2 | Page 1 of 1 |
| APPLICATION NO. | : 10/915912 | |
| DATED | : June 24, 2014 | |
| INVENTOR(S) | : Cao et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1769 days.

Signed and Sealed this
Twenty-fourth Day of March, 2015

Michelle K. Lee
*Director of the United States Patent and Trademark Office*